United States Patent [19]

Taniguchi et al.

[11] Patent Number: 5,110,941

[45] Date of Patent: May 5, 1992

[54] METHODS OF PRODUCING 1H-PYRAOLO(5,1-C)-1,2,4-TRIAZOLES AND PYRAZOLE DERIVATIVES

[75] Inventors: Masato Taniguchi; Tadahisa Sato, both of Minami-ashigara, Japan

[73] Assignee: Fuji Photo Film Co., Ltd., Kanagawa, Japan

[21] Appl. No.: 423,891

[22] Filed: Oct. 19, 1989

[30] Foreign Application Priority Data

Oct. 21, 1988 [JP] Japan .................. 63-265681

[51] Int. Cl.$^5$ ............. C07D 487/04; C07D 417/14; C07D 417/04; C07D 409/14
[52] U.S. Cl. ..................... 548/262.4; 534/752; 544/296; 544/333; 546/256; 546/271; 548/250; 548/251; 548/252; 548/253; 548/254; 548/156; 548/157; 548/159
[58] Field of Search .............. 548/262.4, 110, 111, 548/156, 157, 159, 250, 251, 252, 253, 254; 534/752; 544/296, 333; 546/256, 271

[56] References Cited

U.S. PATENT DOCUMENTS 3,725,067  4/1973  Bailey et al. ............. 548/262.4
4,705,863  11/1987  Sato et al. ............... 548/262.4

FOREIGN PATENT DOCUMENTS 60-197688  10/1985  Japan ................. 548/262.4

Primary Examiner—Patricia L. Morris
Attorney, Agent, or Firm—Birch, Stewart, Kolasch & Birch

[57] ABSTRACT

A method of producing 1H-pyrazolo[5,1-c]-1,2,4-triazoles represented by general formula (II):

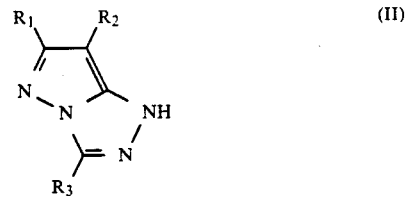

(wherein $R_1$, $R_2$ and $R_3$ each represents a hydrogen atom or a substituent group) which comprises making a compound represented by general formula (I) undergo a ring closure reaction:

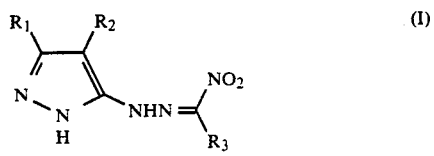

(wherein $R_1$, $R_2$ and $R_3$ each represents a hydrogen atom, or a substituent group), and a method of producing a pyrazol derivative represented by general formula (I) by reacting a compound represented by general formula (III) and general formula (IV):

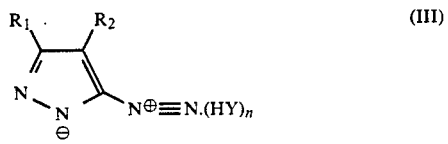

$R_3CH_2NO_2$     (IV)

wherein $R_1$, $R_2$ and $R_3$ have the same meaning as in general formula (I); Y represents an acid radical; and n represents 0 to 1.

7 Claims, No Drawings

METHODS OF PRODUCING 1H-PYRAOLO(5,1-C)-1,2,4-TRIAZOLES AND PYRAZOLE DERIVATIVES

FIELD OF THE INVENTION

The present invention relates to a method of producing 1H-pyrazole[5,1-c]-1,2,4 triazoles which are useful as couplers for silver halide color photography.

BACKGROUND OF THE INVENTION

1H-Pyrazolo[5,1-c]-1,2,4-triazoles are compounds which are useful as couplers, especially magenta couplers, for silver salt color photography. In contrast to conventional pyrazolone type magenta couplers the novel couplers of the present invention are free from color stain attributed to side absorption which the formed dyes have in the vicinity of 430 nm. The utility thereof is described, for example, in JP-B-48-30895 (the term "JP-B" as used herein means an "examined Japanese patent publication"), U.S. Pat. No. 3,725,067, British Patent 1,252,418, *Journal of the Chemical Society*, Perkin I, 2047-2052 (1977), JP-A-62-209457 (the term "JP-A" as used herein means an "unexamined published Japanese patent application"), and JP-A-62-229146.

Methods for synthesizing the foregoing novel couplers are described, for example, in the above-cited *Journal of the Chemical Society*, U.S. Pat. No. 3,725,067, WO 86/01915, JP-A-61-18768, JP-A-62-10068, JP-A-62-10069, JP-A-62-195368, JP-A-62-209457, JP-A-62 228066, JP-A-62-229146 and JP-A-62-252773. Specific examples of methods for synthesizing the couplers include the methods disclosed in the following publications:

1. Journal of the Chemical Society. Perkin I, 2047–2052 (1977)

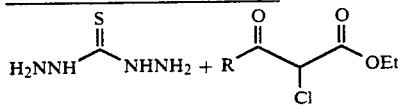

(R = alkyl or aryl)

2. JP-A-62-252773

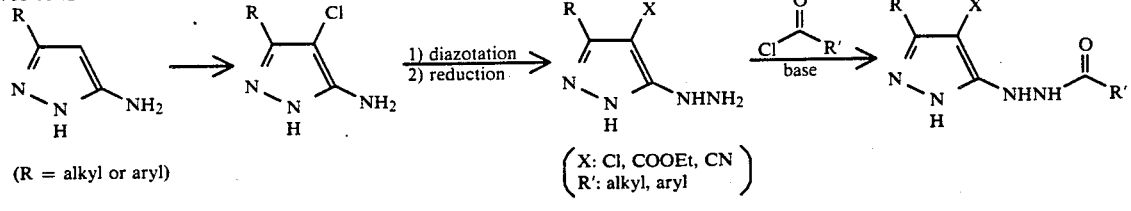

(R = alkyl or aryl)

$\begin{pmatrix} X: Cl, COOEt, CN \\ R': alkyl, aryl \end{pmatrix}$

3. JP-A-62-228066

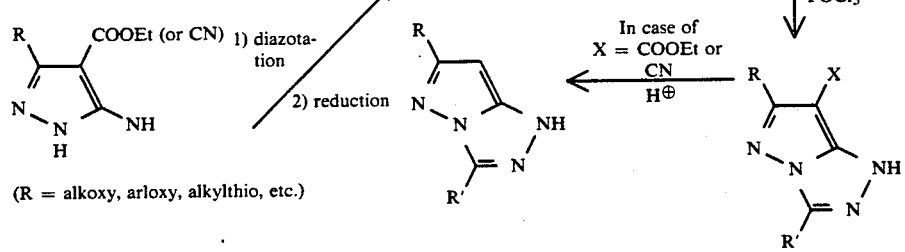

(R = alkoxy, arloxy, alkylthio, etc.)

However, these methods of synthesis suffer from defect(s) such that poisonous thiocarbohydrazide has to be employed as a starting material, a yield rate of the hydrazinopyrazole produced is low, and the produced hydrazinopyrazole can have high solubility in water depending on the kind of substituent R which makes it very difficult to handle. When using 1H-pyrazolo[5,1-c]-1,2,4-triazoles as magenta couplers for photography, additional defects include the fact that the step of eliminating X=COOEt or CN with an acid, the number of steps is increased, and what is worse, the decarboxylation reaction is difficult to control. Moreover, when R is a group other than one which is attached to the pyrazole nucleus via its carbon atom, the hydrazinopyrazole cannot be synthesized at all, or can be synthesized only in a low yield rate.

SUMMARY OF THE INVENTION

An object of the present invention is to provide an inexpensive method of producing 1H-pyrazolo[5,1-c]-1,2,4-triazoles from safe reagents through a reduced number of steps even when a substituent group at the 6-position is attached via an atom other than carbon.

As a result of concentrating intensive studies on the solution of the problems inherent in the above-described methods of synthesis, it has now been found that 1H-pyrazolo[5,1-c]-1,2,4-triazole derivatives can be easily produced by utilizing characteristics of the nitro group which constitutes a nitroalkane compound.

Accordingly, the present invention relates to a method of producing 1H-pyrazolo[5,1-c]-1,2,4-triazoles represented by general formula (II):

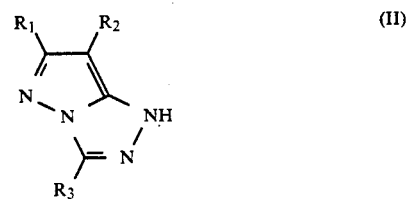

(wherein $R_1$, $R_2$ and $R_3$ each represents a hydrogen atom, or a substituent group) which comprises making a compound represented by general formula (I) undergo a ring closure reaction:

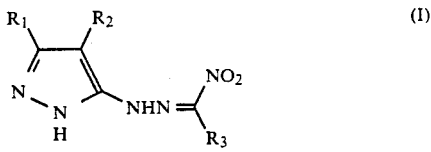

(wherein $R_1$, $R_2$ and $R_3$ each represents a hydrogen atom, or a substituent group).

Further, the present invention relates to a method of producing the 1H-pyrazolo[5,1-c]-1,2,4-triazoles represented by general formula (II), wherein the compound represented by general formula (I) is prepared by reacting a compound represented by general formula (III) with a nitroalkane compound represented by general formula (IV):

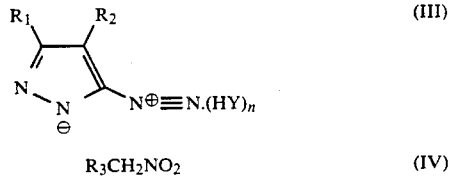

$$R_3CH_2NO_2 \quad (IV)$$

(wherein $R_1$, $R_2$ and $R_3$ have the same meaning as in general formula (I); Y represents an acid radical; and n represents 0 or 1).

Furthermore, the present invention relates to a method of producing the pyrazole derivatives represented by general formula (I), wherein the compounds represented by general formula (III) are made to react with the compounds represented by general formula (IV).

DETAILED DESCRIPTION OF THE INVENTION

Each of the above-illustrated structural formulae (I), (II) and (III), corresponds to only one tautomer out of many imaginable ones. Thus, these structural formulas of the present invention are adopted with the intention of representing all tautomers that each compound can assume.

Detailed descriptions of $R_1$ and $R_2$ in general formulae (I), (II) and (III), those of $R_3$ in general formulae (I), (II) and (IV), and those of Y in general formula (III) are given below.

$R_1$ represents a hydrogen atom or a substituent group, with specific examples thereof including a hydrogen atom, a halogen atom, an aliphatic hydrocarbon group, an aryl group, a heterocyclyl group (preferably a 5- to 7-membered ring containing at least one of N, O and S atom as hetero atom; the same hereinafter), a cyano group, an alkoxy group, an aryloxy group, an acylamino group, an alkylamino group, an anilino group, an ureido group, a sulfamoylamino group, an alkylthio group, an arylthio group, an alkoxycarbonylamino group, a sulfonamido group, a carbomoyl group, a sulfamoyl group, a sulfonyl group, an alkoxycarbonyl group, a heterocyclyloxy group, an azo group, a acyloxy group, a carbamoyloxy group, a silyloxy group, an aryloxycarbonylamino group, an imido group, a heterocyclylthio group, a sulfinyl group, a phosphonyl group, an aryloxycarbonyl group, an acyl group and an azolyl group. These groups can be substituted. In addition, each compound may assume a bis compound which is formed by a divalent group at $R_1$. (In the present invention an acyl group includes an aliphatic and aromatic acyl group, and a sulfonyl group includes an aliphatic and aromatic sulfonyl group).

More specifically, $R_1$ in each compound represents a hydrogen atom; a halogen atom (e.g., chlorine, bromine); an aliphatic hydrocarbon group (including 1-32 carbon straight or branched chain alkyl, aralkyl, alkenyl, alkinyl, cycloalkyl and cycloalkenyl groups, wherein each may be substituted by a group to be attached via its oxygen atom, nitrogen atom, sulfur atom or carbonyl group, hydroxyl group, nitro group, carboxyl group, cyano group or a halogen atom, e.g., methyl, ethyl, propyl, isopropyl, t-butyl, tridecyl, 2-methanesulfonylethyl, 3-(3-pentadecylphenoxy)propyl, 3-[4-{2-[4-(4-hydroxyphenylsulfonyl)phenoxy]-dodecanamido}phenyl]propyl, 2-ethoxytridecyl, trifluoromethyl, cyclopentyl, 3-(2,4-di-t-amylphenoxy)propyl); an aryl group (e.g., phenyl, 4-t-butylphenyl, 2,4-di-t-amylphenyl, 4-tetradecanamidophenyl); a heterocyclyl group (e.g., 2-furyl, 2-thienyl, 2-pyrimidinyl, 2-benzothiazolyl); cyano group; an alkoxy group (e.g., methoxy, ethoxy, 2-methoxyethoxy, 2-dodecylethoxy, 2-methanesulfonylethoxy); an aryloxy group (e.g., phenoxy, 2-methyl phenoxy, 4-t-butylphenoxy, 3-nitrophenoxy, 3-t-butyloxycarbamoylphenoxy, 3-methoxycarbamoylphenoxy); an acylamino group (e.g., acetamido, benzamido, tetradecanamido, α-(2,4-di-t-amylphenoxy)butanamido, γ-(3-t-butyl-4-hydroxyphenoxy)-butanamido, α-{4 (4 hydroxyphenylsulfonyl)phenoxy} decamido); an alkylamino group (e.g., methylamino, butylamino, dodecylamino, diethylamino, methylbutylamino); an anilino group (e.g., phenylamino, 2-chloroanilino, 2-chloro 5 tetradecanaminoanilino, 2-chloro-5-dodecyloxycarbonylanilino, N-acetylanilino, 2-chloro-5-{α-(3-t-butyl-4-hydroxyphenoxy) dodecanamido}anilino); an ureido group (e.g., phenylureido, methylureido, N,N-dibutylureido); a sulfamoylamino group (e.g., N,N-dipropylsulfamoylamino, N-methyl N-decylsulfamoylamino); an alkylthio group (e.g., methylthio, octylthio, tetradecylthio, 2-phenoxyethylthio, 3-phenoxypropylthio, 3-(4-t-butyl-phenoxy)propylthio); an arylthio group (e.g., phenylthio, 2-butoxy-5-t-octylphenylthio, 3-pentadecylphenylthio, 2-catboxyphenylthio, 4-tetradecanamidophenylthio); an alkoxycarbonylamino group (e.g., methoxycarbonylamino, tetradecyloxycarbonylamino); a sulfonamido group (e.g., methanesulfonamido, hexadecane sulfonamido, benzenesulfonamido, p-toluenesulfonamido, octadecanesulfonamido, 2-methyloxy-5-t-butylbenzenesulfonamido); a carbamoyl group (e.g., N-ethylcarbamoyl, N,N-dibutylcarbamoyl, N-(2-dodecyloxyethyl)carbamoyl, N-methyl-N-dodecylcarbamoyl, N-{3-(2,4-di-t-amylphenoxy)-propyl}carbamoyl); a sulfamoyl group (e.g., N-ethylsulfamoyl, N,N-dipropylsulfamoyl, N-(2-dodecyloxyethyl)-sulfamoyl, N-ethyl-N-dodecylsulfamoyl, N,N-diethylsulfamoyl); a sulfonyl group (e.g., methanesulfonyl, octanesulfonyl, benzenesulfonyl, toluenesulfonyl); an alkoxycarbonyl group (e.g., methoxycarbonyl, butyloxycarbonyl, dodecyloxycarbonyl, octadecyloxycarbonyl); a heterocycloxy group (e.g., 1-phenyltetrazole-5-oxy, 2-tetrahydropyranyloxy); an azo group (e.g., phenylazo, 4-methoxyphenylazo, 4-pivaloylaminophenylazo, 2-hydroxy-4-propanoylphenylazo); an acyloxy group (e.g., acetoxy); a carbamoyloxy group (e.g., N-methylcarbamoyloxy, N-phenylcarbamoyloxy); a silyloxy group (e.g., trimethylsilyloxy, dibutylmethylsilyloxy); an aryloxycarbonylamino group (e.g., phenoxycarbonylamino); an imido group (e.g., N-succinimido, N-phthalimido, 3-octadecenylsuccinimido), a heterocyclthio group (e.g., 2-benzothiazolylthio, 2,4-di-phenoxy-1,3,5-triazole-6-thio, 2-pyridylthio); a sulfinyl group (e.g., dodecanesulfinyl, 3-pentadecylphenylsulfinyl, 3 phenoxypropylsulfinyl,); a phosphonyl group (e.g., phenoxyphosphonyl, octyloxyphosphonyl, phenylphosphonyl); an aryloxycarbonyl group (e.g., phenoxycarbonyl); an acyl group (e.g., acetyl, 3-phenylpropanoyl, benzoyl, 4-dodecyloxybenzoyl), or an azolyl group (e.g., imidazolyl, pyrazolyl, 3-chloropyrazole-1-yl, triazolyl).

Among these substituent groups, those preferred as $R_1$ include an alkyl group, an aryl group, an alkoxy group, an aryloxy group, an alkylthio group, an ureido group, an alkoxycarbonylamino group, an aryloxycarbonylamino group and an acylamino group.

$R_2$ includes the same substituent groups as cited above as examples of $R_1$, and those preferred as $R_2$ include a halogen atom, an alkyloxy group, an aryloxy group, an alkylthio group, an arylthio group, an azo group and an azolyl group.

$R_3$ includes the same substituent groups as cited above as examples of $R_1$, and those preferred as $R_3$ are specifically a hydrogen atom, an alkyl group, an aryl group, a heterocyclyl group, an alkoxy group, an aryloxy group, an alkylthio group, an arylthio group, an alkoxycarbonyl group, a carbamoyl group and a cyano group. Of these groups, a hydrogen atom, an alkyl group, an aryl group and a heterocyclyl group are preferred.

Y represents an inorganic or an organic acid radical. Suitable examples of an inorganic acid radical include hydrochloric acid radical, hydrobromic acid radical, sulfuric acid radical, nitric acid radical and so on, and examples of an organic acid radical include acetic acid radical, trifluoroacetic acid radical, trichloroacetic acid radical, dichloroacetic acid radical, methanesulfonic acid radical, trifluoromethanesulfonic acid radical, benzenesulfonic acid radical, p-toluenesulfonic acid radical and so on.

Pyrazolo[5,1-c]-1,2,4-triazole compounds represented by general formula (II) in the present invention are mainly employed as magenta couplers for photography. However, it is to be understood herein that their use is not limited to the above-described one. Therefore, a group capable of splitting off upon the reaction with the oxidation product of a developing agent (which is hereinafter simply called a splitting off group) has considerable significance as the group represented by $R_2$, but $R_2$ may be converted to a splitting-off group afterwards. So far as the method of synthesis for the present invention are concerned, it goes without saying that $R_2$ may or may not be a splitting-off group.

Specific examples of 1H-pyrazolo[5,1-c]-1,2,4-triazoles represented by general formula (II) which can be synthesized by the methods of the present invention are illustrated below. However, the invention should not be construed as being limited to these representative examples.

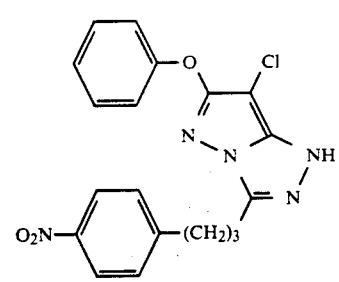

(1)

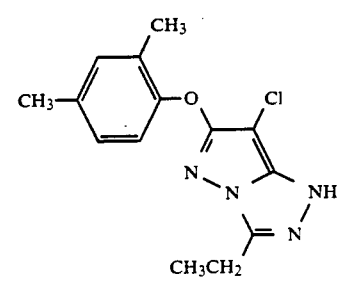

(2)

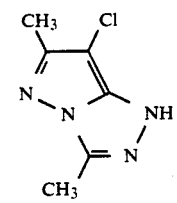

(3)

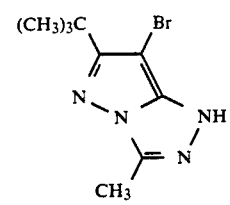

(4)

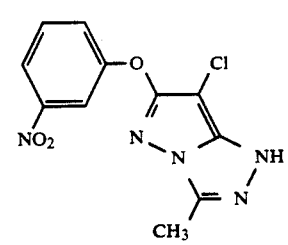

(5)

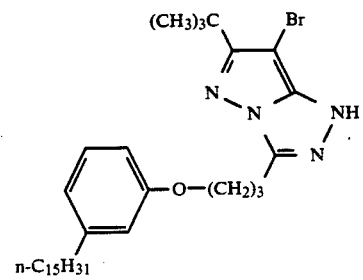

(6)

-continued
(7)
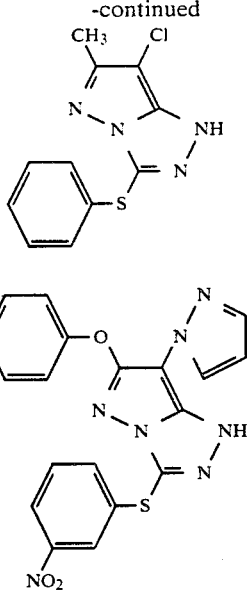
(8)
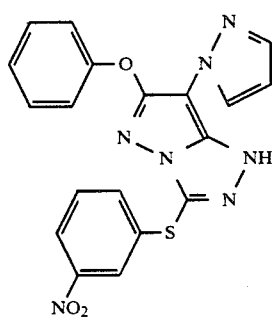
(9)
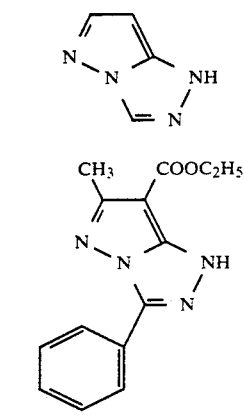
(10)
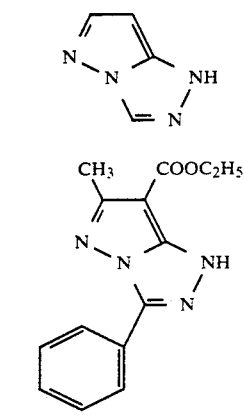
(11)
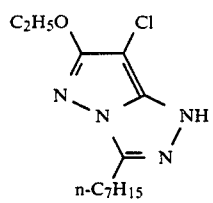
(12)
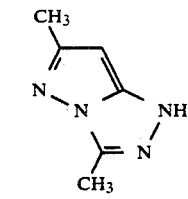
(13)
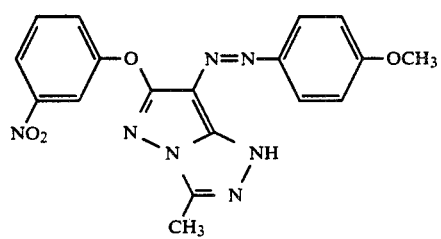
-continued
(14)
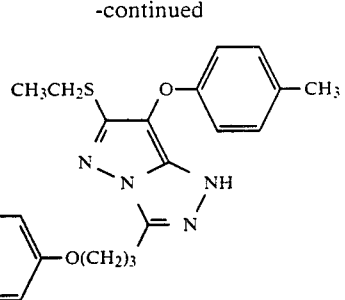
(15)
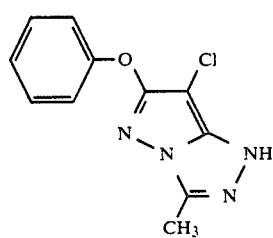
(16)
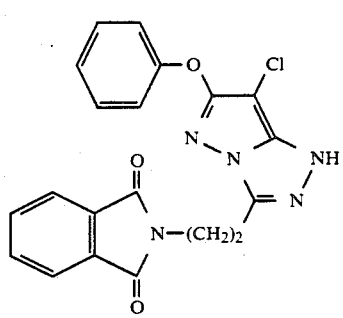
(17)
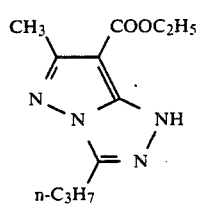
(18)
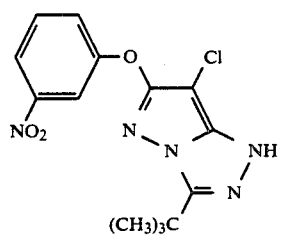
(19)
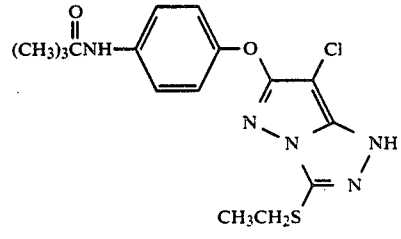

-continued
(20) 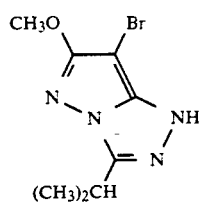
(21) 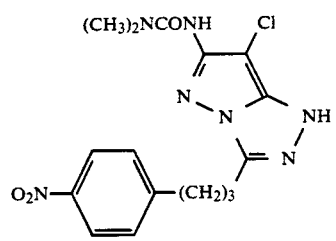
(22) 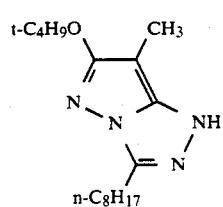
(23) 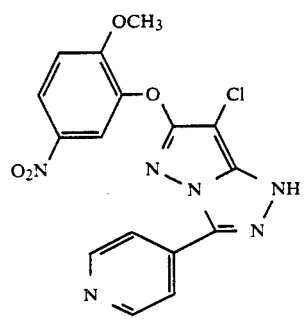
(24) 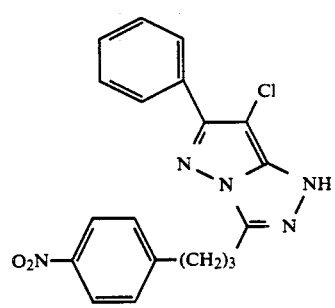
(25) 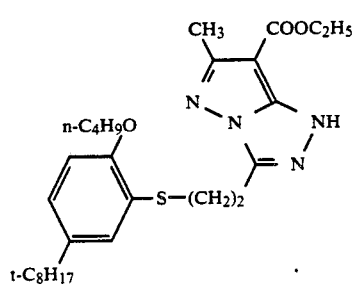
-continued
(26) 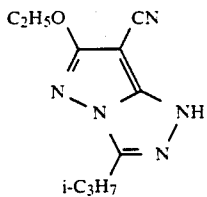
(27) 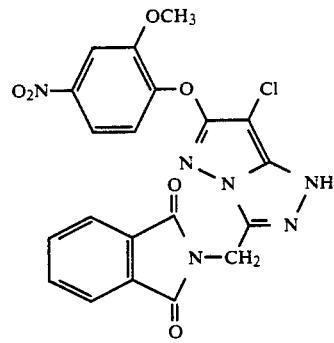
(28) 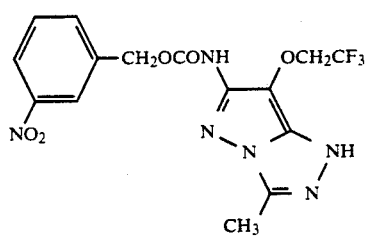
(29) 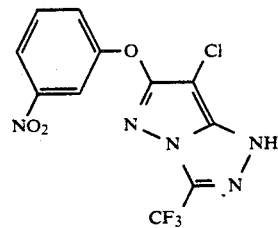
(30) 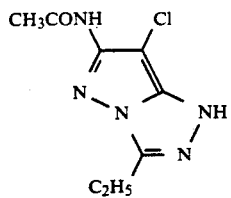
(31) 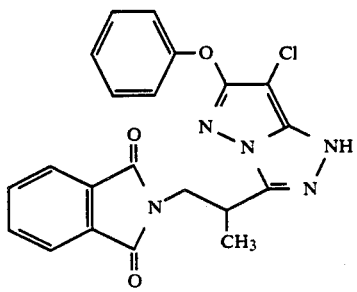

-continued
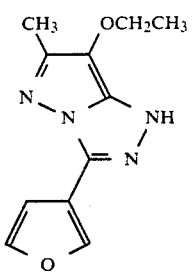 (32)
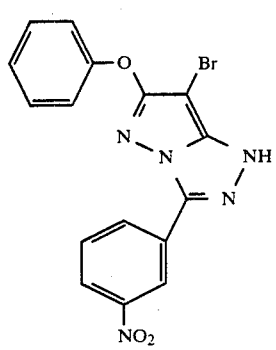 (33)
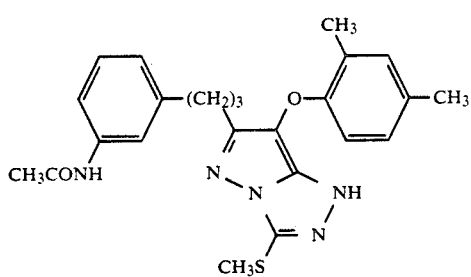 (34)
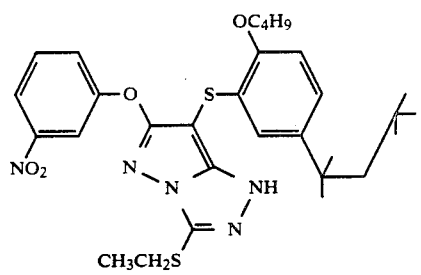 (35)
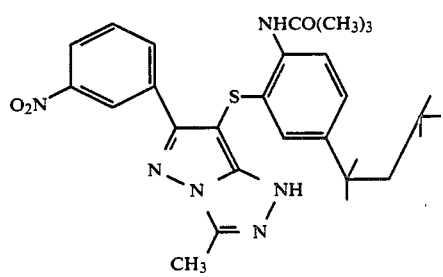 (36)
-continued
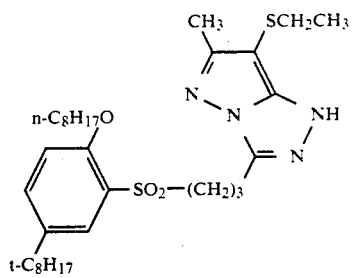 (37)
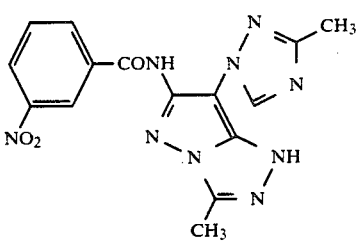 (38)
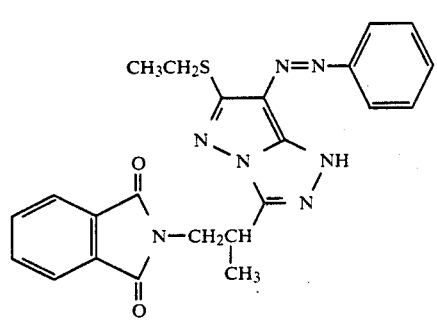 (39)
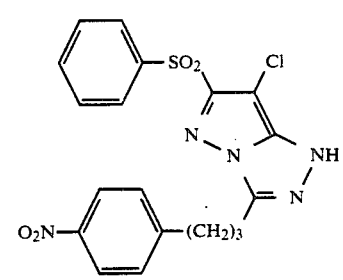 (40)
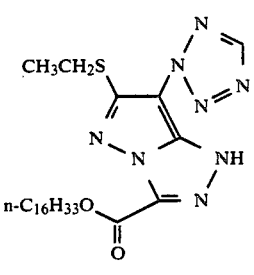 (41)
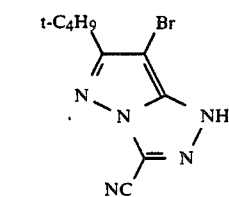 (42)

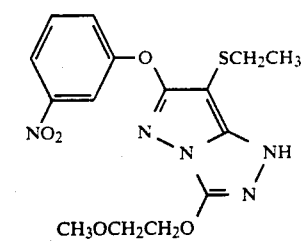

(43)

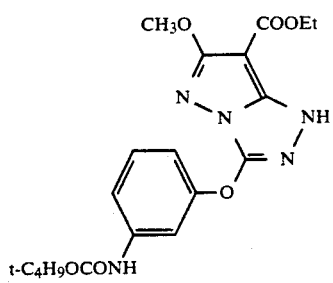

(44)

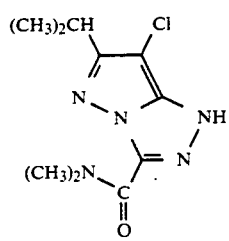

(45)

Now, various embodiments of the present invention are described below in detail.

The synthesis process of the present invention is shown using reaction steps represented by scheme (1):

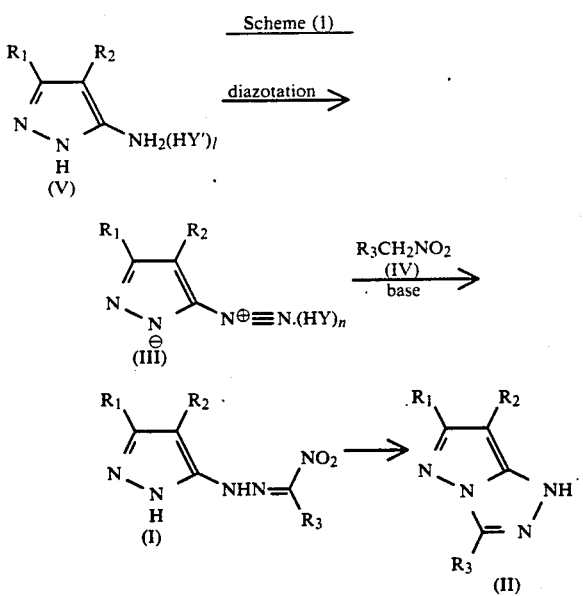

In the above reaction scheme (1), $R_1$, $R_2$, $R_3$ and Y in general formulae (I), (II), (III) and (IV) have the same meaning as described hereinbefore, respectively. $R_1$ and $R_2$ in general formula (V) have the same meaning as in the general formula (III), respectively. Y', though it has the same meaning as Y, may be the same as or different from Y. represents 0 or 1, and n also represents 0 or 1.

The compounds represented by general formula (III) can be synthesized in accordance with the methods illustrated, for example, in *Chemical Reviews*, vol. 75, No. 2. pp. 241 to 257 (1975), *Journal of Heterocyclic Chemistry*, vol, 18, p. 675 (1981), *Chemische Berichte*, vol. 117, pp. 1726 to 1747 (1984), JP-A-62-10068, JP-A-62-10069, JP-A-62-195368, JP-A-62-228066, JP-A-62-229146 and JP-A-62-252773, and the methods described in the references cited from the above-described publications and patent specifications.

The compounds represented by general formula (III) are obtained in the form of a solution in water or in an organic solvent, usually containing excess HY, or in the form of solution in HY itself when HY is an organic acid which is in a liquid state at room temperature. These compounds correspond to the case of n=1 in general formula (III). These solutions may be used in the subsequent reaction of the present invention as they are, or after conversion to the diazoazole compounds corresponding to the case of n=0 by a neutralization treatment according to a conventional method, they may be used in the reaction of this invention.

The aminopyrazoles represented by general formula (V) can be synthesized in accordance with the methods described, for example, in the above-cited patents, publications, and references quoted therefrom, and also JP-B-45-22328 (the term "JP-B" as used herein means an "examined Japanese patent publication"), JP-B-48-2541, *Takeda Kenkyusho Ho*, 30, 475 (1971) and JP-A-62-209457.

The derivation to the diazonium salts represented by general formula (III) from the aminopyrazoles represented by general formula (V) can be effected in accordance with such a known method as to use, for example, sodium nitrite, isoamyl nitrite or the like.

The nitroalkane compounds represented by general formula (IV) are readily available depending on the kind of $R_3$ (e.g., when $R_3$ is a hydrogen atom, a methyl group, an ethyl group or the like), or can be easily synthesized according to conventional methods described, for example, in *Journal of the American Chemical Society*, 76, 3209 (1954), *Supra*, 78, 1497 (1956), *Journal of Organic Chemistry*, 22, 455 (1957), *Supra*, 43, 3101 (1978), *Journal of the Chemical Society Chemical Communication*, 362 (1978).

The reaction of synthesizing the compounds represented by general formula (I) from the compounds represented by general formula (III) and the compounds represented by general formula (IV) is described below in detail.

The compounds represented by general formula (IV) are preferably used in an amount of from 0.5 to 5 equivalents, particularly from 0.8 to 3.0 equivalents, relative to the compounds represented by general formula (III).

The reaction solvent to be used may be chosen from any type of solvent, whether it is protic or aprotic, and whether it has high polarity or not, if desired. The solvent may be a mixture of two or more different types of solvents.

Examples of preferred reaction solvents include sulfone solvents such as sulforan, etc., sulfoxide solvents such as dimethyl sulfoxide, etc., amide solvents such as N,N-dimethylformamide, N,N-dimethylacetamide, etc., urea solvents such as N,N,N',N'-tetramethylurea, etc., alcohol solvents such as methanol, ethanol, isopropyl alcohol, tert-butanol, etc., ether solvents such as tetrahydrofuran, dioxane, etc., halogenated hydrocarbon solvents such as methylene chloride, chloroform, dichloroethane, etc., basic solvents such as triethylamine, pyridine, etc., nitrile solvents such as acetonitrile, etc., aromatic hydrocarbons such as benzene, toluene, xylene, etc., and so on. Of these solvents, alcohol solvents and aide solvents such as N,N-diemthylformamide and N,N-dimethylacetamide are preferred over the others.

A preferred reaction temperature range is from $-20°$ C. to 100° C., and more particularly is from $-10°$ C. to 40° C.

Bases which may be used are those capable of dissociating a proton located at the α-position of the nitroalkane. Suitable examples thereof include metal hydroxides such as sodium hydroxide, potassium hydroxide, etc., metal salts of alcohols such as sodium methoxide, potassium tert-butoxide, etc.; metal hydrides such as sodium hydride, etc., organometallic compounds such as butyl lithium, methylmagnesium iodide, etc.; metal amide compounds such as lithium diisopropylamide, etc.; alkali metals such as sodium, potassium, etc., and organic bases such as pyridine, triethylamine, etc. Of these bases, sodium hydroxide, sodium methoxide and sodium hydride are preferred over the others.

Although the amount of a base to be used depends on the basicity thereof, it is desirable that the base should be used in an amount which is enough to render the pH of the reaction system within the range of from 7 to 14 even at the conclusion of that reaction.

The reaction time is preferably in the range of from 5 minutes to 10 hours, and more preferably is from 5 minutes to 3 hours. However, the reaction conditions employable herein should not be construed as being limited to the above-described conditions.

Some of the thus obtained compounds of general formula (I) are difficult to isolate because of their instability. In such cases, the reaction product may be subjected to the next reaction as it is without being isolated.

Finally, the reaction for synthesizing the compounds represented by general formula (II) from the compounds represented by general formula (I) is described below in detail.

The synthesis of the compounds of general formula (II) through the ring closure reaction of the compounds of the general formula (I) is preferably carried out in the presence of a base.

Bases which may be used in the above-described synthesis include inorganic and organic ones, preferably those bases capable of dissociating a proton situated in the α-position of the nitroalkanes, and more preferably sodium hydroxide, sodium methoxide, and so on.

A suitable quantity of the base which may be used is in the range of 0.5 to 5 equivalents, and preferably is in the range of 0.8 to 3 equivalents with respect to the compound represented by formula (I).

Reaction solvents which may be used in this reaction include water, and those solvents used for the synthesis of the compounds of general formula (III), preferably water and alcoholic solvents.

The reaction temperature is preferably in the range of from 10° C. to 150° C., more preferably is from room temperature to 120° C., and particularly preferably is from room temperature to 100° C.

The reaction time is preferably in the range of from 15 minutes to 48 hours, more preferably is from 30 minutes to 24 hours, and particularly preferably is from 30 minutes to 12 hours. However, this reaction should not be construed as being limited to these conditions.

Although 1H-pyrazolo[1,5-c]-1,2,4-triazole derivatives prepared by the reaction steps represented by scheme (1) can be separated from the reaction solution in a conventional manner, they can be used as a starting material of a subsequent reaction without undergoing any isolation step, if desired. Examples of isolation means which can be properly used include the usual recrystallization techniques, solvent extraction, filtration, column chromatography, thin layer chromatography and so on. These techniques may be employed independently or in combination.

In accordance with the method of this invention, 1H-pyrazolo[1,5-c]-1,2,4 triazole derivatives represented by general formula (II) can be synthesized in a shortened process, compared with conventional methods. In addition, 1H-pyrazolo[1,5-c]1,2,4-triazoles having various kinds of substituent groups at their respective 6-positions can be easily synthesized.

Accordingly, synthesizing costs can be reduced and, at the same time, replacement of a substituent group located at the 6-position can be facilitated, resulting in an enhancement of the utility value of these 1H-pyrazolo[1,5-c]-1,2,4-triazole derivatives as photographic couplers.

The present invention will now be illustrated in greater detail by reference to the following examples. However, the invention should not be construed as being limited to these examples.

Example 1

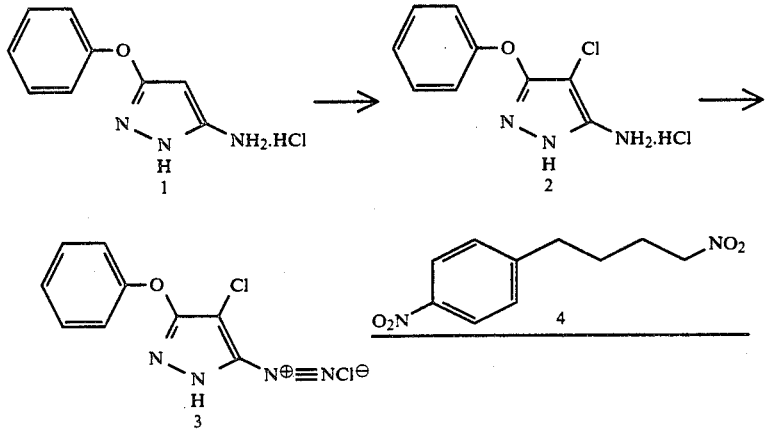

-continued

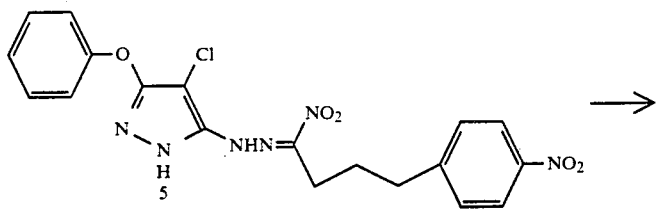

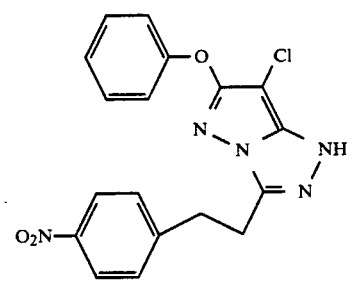

Exemplified Compound (1)

A 38 ml portion of 36% hydrochloric acid was added to 8.61 g ($4.07\times10^{-2}$ mol) of 5-amino-3-phenoxypyrazole hydrochloride (1), and cooled in an ice bath. 3.43 ml ($4.27\times10^{-2}$ mol) of sulfuryl chloride was slowly added dropwise thereto while stirring to synthesize compound 2. The reaction solution was stirred for an additional one hour as it was, and a solution of 2.95 g ($4.27\times10^{-2}$ mol) of sodium nitrite in 5.9 ml of water wa gradually added dropwise thereto. The reaction mixture was further stirred for 1.5 hours, resulting in the production of compound 3. A solution of the thus produced compound 3 was slowly added dropwise to a solution while stirring and cooling with ice, said solution having been prepared by adding 102 ml of 28% sodium methylate to a solution of 9.58 g ($4.27\times10^{-1}$ mol) of compound 4 in 177 ml of ethanol while stirring and cooling with ice (during the addition, the reaction solution turned dark orange), and the stirring was further continued for 1 hour (to synthesize the compound 5). Then, the reaction solution was heated while stirring under reflux for 1.5 hours. Thereafter, ethanol was distilled away from the reaction solution under reduced pressure, and the residue was dissolved in chloroform, washed with a saturated aqueous solution of sodium chloride, dried over Glauber's salt, and chloroform was distilled away under reduced pressure. The residue was purified by column chromatography (eluate: chloroform/ethyl acetate), and further by recrystallization from a chloroform/hexane mixture to yield 6.90 g of the exemplified compound (1) as a colorless crystal (yield rate: 43% based on compound 1). Data of physical properties of the thus produced exemplified compound (1) are shown below.

Melting Point: 155° to 156.5° C.

$^1$H-NMR Spectrum (CDCl$_3$): $\delta$=2.23 (m, 2H), 2.82 (t, 2H), 2.96 (t, 2H), 7.1 to 7.4 (m,7H), 8.12 (d, 2H), 9.18 (brs. 1H).

Mass Spectrum: m/e 397 (M$^+$)

Finally, the compound 4 was synthesized from compound a, which had been prepared from γ-lactone and benzene in a known manner, according to the method described in *Journal of the American Chemical Society*, vol. 76, p. 3209 (1954)

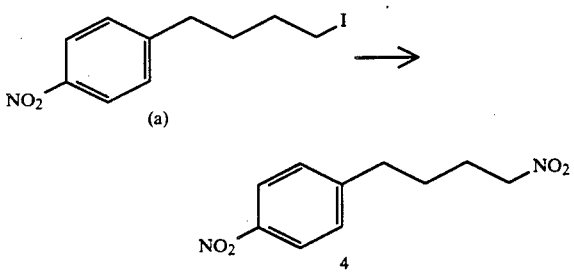

EXAMPLE 2

Synthesis of Exemplified Compound (2)

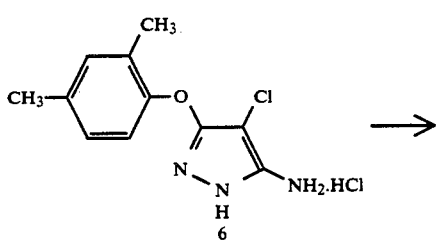

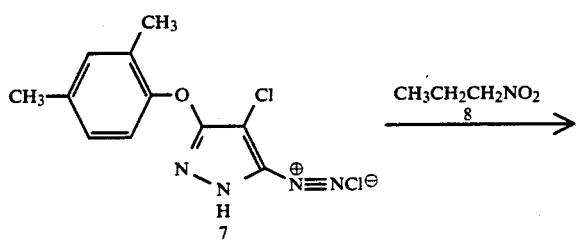

-continued

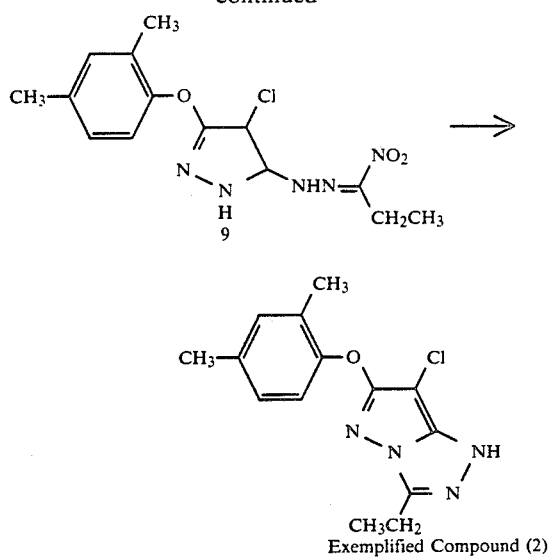

Exemplified Compound (2)

An 8.6 ml portion of 36% hydrochloric acid was added to 1.05 g (3.83 mmol) of 5-amino-4-chloro-3-(2,4-dimethylphenoxy)pyrazole hydrochloride (6) under cooling. A solution of $2.9 \times 10^{-1}$ g (4.21 mmol) of sodium nitrite in 0.6 ml of water was slowly added dropwise thereto, and was stirred for an additional one hour to synthesize compound 7. Then, a solution of the thus produced compound 7 was slowly added dropwise to a reactant solution, which had been prepared by adding 3.98 g ($9.96 \times 10^{-2}$ mol) of sodium hydroxide to a methanol solution containing $3.6 \times 10^{-1}$ g (4.02 mmol) of compound 8, while stirring and cooling with ice. The reaction mixture was stirred for an additional one hour. During the addition, the reaction solution turned dark orange. Thereafter, ethanol was distilled away from the reaction solution under reduced pressure, and the residue was dissolved in ethyl acetate, washed with a saturated aqueous solution of sodium chloride, and dried over Glauber's salt. Ethyl acetate was distilled therefrom under reduced pressure to obtain 1.60 g of solid containing compound 9. This solid (containing 1.60 g of compound 9) was dissolved in 40 ml of ethanol, and heated while stirring under reflux for 2 hours. Thereafter, ethanol was distilled away under reduced pressure, and the residue was admixed with ethyl acetate, washed with a saturated aqueous solution of sodium chloride, and dried over Glauber's salt. Ethyl acetate was distilled away under reduced pressure, and the solid obtained was recrystallized from a chloroform/hexane mixture to obtain 0.28 g of a colorless, crystalline compound (exemplified compound (2)). The yield rate was 25% based on compound 6. Data of physical properties of the thus produced exemplified compound (2) are shown below.

Melting Point: 150° to 153°

$^1$H-NMR Spectrum (DCDl$_3$): $\delta$=1.38 (t, 3H), 2.24 (s, 3H), 2.31 (s, 3H), 2.90 (q, 2H), 6.9 to 7.1 (m, 3H), 9.43 (brs. 1H).

Mass Spectrum: m/e 290 (M+)

EXAMPLE 3

Synthesis of Exemplified Compound (3)

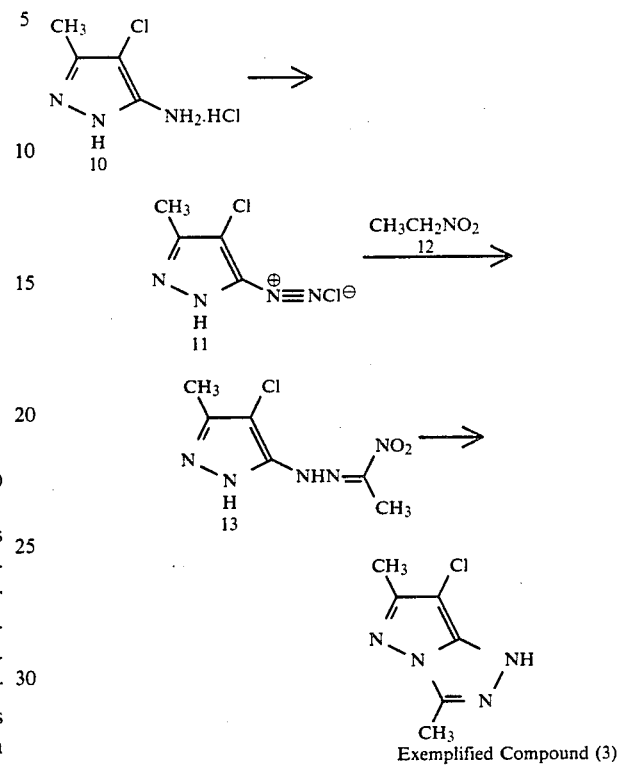

Exemplified Compound (3)

A 51 ml portion of 36% hydrochloric acid was added to 8.56 g ($5.09 \times 10^{-2}$ mol) of 5-amino-3-methylpyrazole hydrochloride (10), and a solution of 3.69 g ($5.35 \times 10^{-2}$ mol) of sodium nitrite in 7.4 ml of water was added dropwise thereto over a 30-minute period while stirring and cooling with ice. The reaction mixture was further stirred for 1 hour. The thus obtained solution containing compound 11 was named Solution (1). Solution (1) was added dropwise over a 35-minute period to a reactant solution, which had been prepared by adding 7.32 ml ($1.02 \times 10^{-1}$ mol) of nitroethane (12) to a solution of 26.5 g ($6.62 \times 10^{-1}$ mol) of sodium hydroxide in a mixture of 106 ml of ethanol with 53 ml of water while stirring and cooling in an ice bath, and then stirring the admixture for 30 minutes. The resulting reaction mixture was stirred for an additional 2 hours as it was cooled in an ice bath. During the stirring, the reaction solution turned dark orange (to produce compound 13). Then, the reaction solution was heated while stirring under reflux for 2.5 hours. Thereafter, ethanol was distilled away from the reaction solution under reduced pressure, and the residue was extracted with ethyl acetate, washed with a saturated aqueous solution of sodium chloride, and dried over Glauber's salt. Ethyl acetate was distilled therefrom under reduced pressure to yield 7.0 g of the exemplified compound (3) as crude crystals (crude yield rate: 81% based on compound 10). These crude crystals were purified by silica gel column chromatography (eluate: chloroform/methanol), and further by recrystallization from hot acetonitrile to yield 2.20 g of exemplified compound (3) as colorless crystals (yield rate: 25% based on compound 10). Data of the physical properties of the thus produced exemplified compound (3) are shown below.

Melting Point: decomposed at 202° to 238° C. (in a sealed tube)

$^1$H-NMR Spectrum (CDCl$_3$): γ=2.38 (s, 3H), 2.59 (s, 3H), 9.30 (brs. 1H).

Mass Spectrum: m/e 170 (M+)

EXAMPLE 4

Synthesis of Exemplified Compound (4)

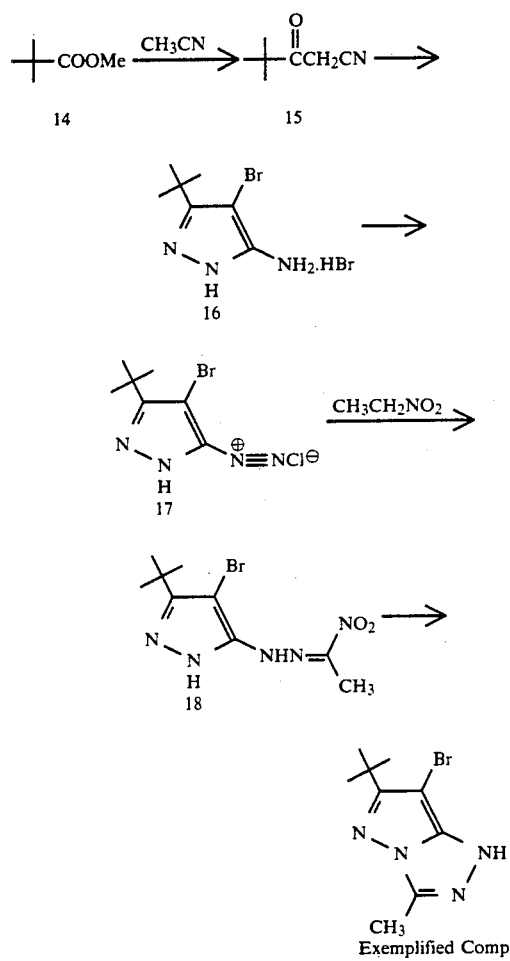

Exemplified Compound (4)

Synthesis of Compound 15

A mixture of 255 g (2.20 mol) of compound 14, 180 g (4.40 mol) of acetonitrile and 200 ml of tetrahydrofuran was added dropwise for a one-hour period to a solution of 322 g (2.42 mol) of t-butoxy potassium in 1.3 liters of tetrahydrofuran while heat-refluxing and stirring, and then heated while stirring under reflux for 4 hours.

Thereafter, the reaction solution was poured into water, and the pH thereof was adjusted to below 7 by adding 36% hydrochloric acid. The reaction product was extracted with ethyl acetate, and dried over Glauber's salt. Then, ethyl acetate was distilled away therefrom under reduced pressure. Thus, 190 g of compound 15 was obtained as crude crystal.

Synthesis of Compound 16

1.5 Liters of ethanol and 500 ml of isopropanol were added to 190 g (1.52 mol) of the crude crystal of compound 15, and 114 g (1.82 mol) of hydrazine monohydrate was further added dropwise at room temperature while stirring. The resulting mixture was heated while stirring under reflux for 6 hours. Thereafter, the insoluble matter was filtered out, and from the filtrate ethanol and isopropanol were distilled away under reduced pressure. To 213 g of the thus obtained residue was added 800 ml of glacial acetic acid, and 245 g (1.53 mol) of bromine was further added dropwise while stirring at a temperature of below 30° C. The reaction mixture was stirred for an additional one hour.

Thereafter, the insoluble matter was filtered out, and the acetic acid was distilled away from the filtrate under reduced pressure. The resulting residue was recrystallized from hot ethyl acetate to obtain 343 g of compound 16 as pale yellow crystal (yield rate: 52% based on compound 14). Data of the physical properties of the thus obtained compound 16 are shown below.

Melting Point: 178° to 183.5° C.

$^1$H-NMR Spectrum (DMSO-d$_6$): γ=1.37 (s, 9H), 9.95 (brs. 4H).

Mass Spectrum: m/e 217, 219 (M+, 1:1)

Elemental Analysis:

Calcd. (as C$_7$H$_{13}$N$_3$Br$_2$): C 28.12; H 4.38; N 14 05; Br 53.45.

Found : C 28.06; H 4.16; N 14.17; Br 53.37.

Synthesis of Compound 18

A 90 ml portion of 36% hydrochloric acid was added to 26.9 g ($8.98 \times 10^{-2}$ mol) of compound 16, and slowly added dropwise thereto was a solution of 6.51 g ($9.43 \times 10^{-2}$ mol) of sodium nitrite in 13 ml of water while stirring and cooling with ice. The reaction mixture was further stirred for 2 hours. The thus obtained solution containing compound 17 was named Solution (1). Solution (1) was added dropwise over a 30-minute period to a reactant solution, which had been prepared by adding 12.9 ml ($1.79 \times 10^{-1}$ mol) of nitroethane to a solution of 46.7 g (1.17 mol) of sodium hydroxide in a mixture o 187 ml of dimethylformamide with 93 ml of water while stirring and cooling with ice, and then stirring the admixture for 30 minutes (during the stirring, white precipitates separated out of the reaction solution). The resulting reaction mixture was stirred for an additional 40 minutes while cooling with ice. During the stirring, the reaction solution turned dark orange. Thereafter, the reaction solution was adjusted to a pH of about 5 by the addition of 12 ml of 36% hydrochloric acid, and then water was added to precipitate crystals. These crystals were filtered off, and the filtrate was extracted once with ethyl acetate. The separated crystals were added to the extract, and dissolved therein. The resulting solution was washed with a saturated aqueous solution of sodium chloride, and dried over Glauber's salt. Ethyl acetate was distilled away under reduced pressure, and the thus obtained residue was recrystallized from an ethyl acetate/hexane mixture to yield 18.4 g of compound 18 as orange crystals (crude yield rate: 67% based on compound 16). Data of physical properties of the thus produced compound 18 are shown below.

Melting Point: 119° to 121° C. (decomposed)

$^1$H-NMR Spectrum (CDCl$_3$): γ=1.40 (s, 9H), 2.44 (s, 3H), 12.09 (brs. 1H).

Mass Spectrum: m/e 303, 305 (M+, 1:1)

Elemental Analysis

Calcd. (as C$_9$H$_{14}$N$_5$O$_2$Br): C 35.44; H 4.64; N 23.03; Br 26.27.

Found : C 35.41; H 4.49; N 23.12; Br 26.29.

Synthesis of Exemplified Compound (4)

A 6.7 ml portion of 28% sodium methylate was added to a solution of 5.07 g (1.67×10⁻² mol) of compound 18 in 76 ml ethanol, and heated while stirring under reflux for 8 hours. Thereafter, the reaction mixture was diluted with water, and then methanol and ethanol were distilled away therefrom under reduced pressure. The resulting residue was dissolved in ethyl acetate, washed with a saturated aqueous solution of sodium chloride, and dried over Glauber's salt. Ethyl acetate was distilled away therefrom under reduced pressure. The thus obtained residue was purified by silica gel column chromatography (eluate: hexane/ethyl acetate) to yield 2.80 g of the exemplified compound (4) as pale yellow crystals (yield rate: 65% based on compound 18). Further, these crystals were recrystallized from hot acetonitrile to obtain 1.35 g of exemplified compound (4) as colorless crystals (yield rate: 31.5% based on compound 18). Data of physical properties of the thus produced compound (4) are shown below.

Melting Point: 182° to 189° C. (decomposed)

$^1$H-NMR Spectrum (CDCl$_3$): $\gamma$=1.49 (s, 9H), 2.62 (s, 3H), 9.41 (brs. 1H).

Mass Spectrum: m/e 251, 253 (M$^+$, 1:1)

Elemental Analysis

Calcd. (as C$_9$H$_{13}$N$_4$Br):C 42.04; H 5.10; N 21.79; Br 31.07.

Found : C 42.02; H 4.98; N 21.82; Br 31.06.

EXAMPLE 5

Synthesis of Exemplified Compound (5)

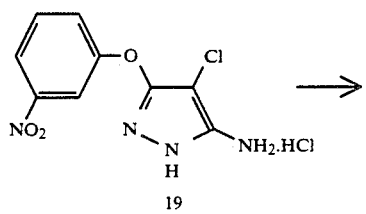
19

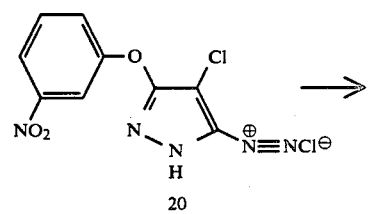
20

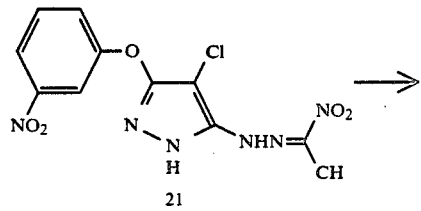
21

-continued

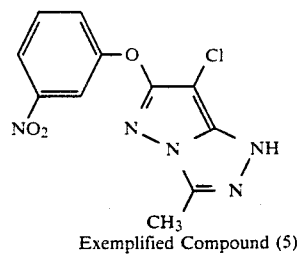
Exemplified Compound (5)

3 ml of methanol and 2.86 ml of 36% hydrochloric acid were added to 1.00 g (3.44 mmol) of compound 19, and 0.51 ml (3.78 mmol) of isoamyl nitrite was further added while stirring and cooling with ice. The reaction mixture was stirred for an additional 2.5 hours, and then the precipitated crystals were filtered off, and washed with water. These crystals (compound were added to a mixture of 0.49 ml (6.87 mmol) of nitroethane, 1.38 ml of 28% sodium methylate and 10 ml of ethanol while stirring and cooling with ice, and then further stirred for 2 hours. (During the stirring, the reaction solution turned dark orange to produce compound 21). Then, the reaction solution was heated while stirring under reflux for 2.5 hours.

Thereafter, ethanol was distilled away from the reaction solution under reduced pressure, and the residue was dissolved in ethyl acetate, washed with a saturated aqueous solution of sodium chloride, and dried over Glauber's salt. Ethyl acetate was distilled away under reduced pressure to obtain an oily matter containing 0.82 g of exemplified compound (5). The thus obtained oily matter was purified by silica gel column chromatography (eluate: hexane/ethyl acetate), and further by recrystallization from hot acetonitrile to yield 54 mg of exemplified compound (5) (yield rate: 5.3% based on compound 19). Data of properties of the thus produced exemplified compound (5) are shown below.

Melting Point: 202° to 205° C. (decomposed)

$^1$H-NMR Spectrum (DMSO-d$_6$): $\gamma$=2.10 (s, 3H), 7.6 to 7.8 (m, 2H), 7.99 (s, 1H), 8.07 (d, 2H), 13.34 (brs. 1H).

Mass Spectrum: m/e 293 (M$^+$, 1:1)

EXAMPLE 6

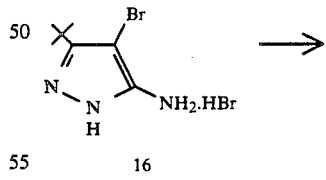
16

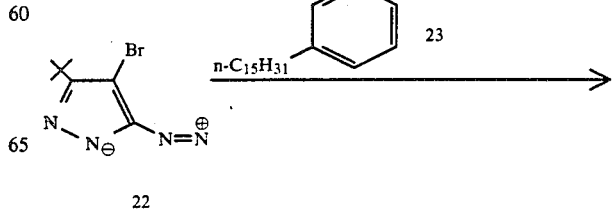
22    23

-continued

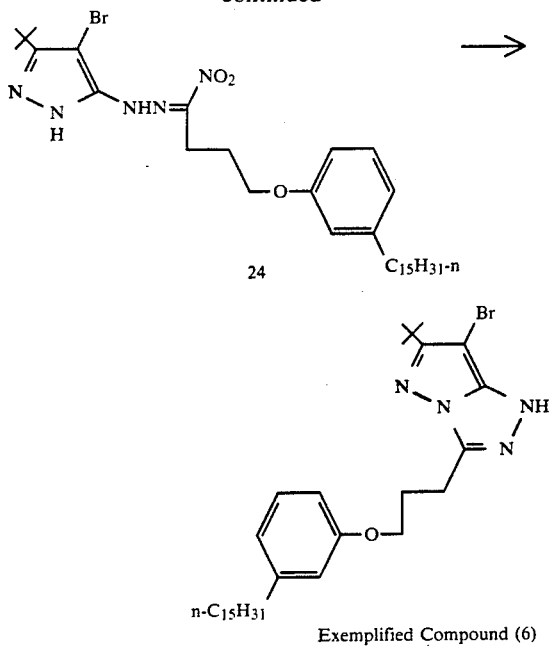

24

Exemplified Compound (6)

A solution of 0.56 g (8.11 mmol) of sodium nitrite in 1.2 ml of water was added dropwise to a solution of 2.31 g (7.73 mmol) of compound 16 in 7.7 ml of 36% hydrochloric acid, and the stirring was continued for one hour. 30 ml of methylene chloride was added to the reaction mixture, and further a suspension of 9.3 g ($1.11 \times 10^{-2}$ mol) of sodium hydrogen carbonate in 30 ml of water was added to adjust the pH to about 7 and to separate the mixture into liquid phases. After the methylene chloride phase was dried over Glauber's salt, the salt was filtered out to obtain a methylene chloride solution of compound 22.

0.22 g (9.27 mmol) of sodium hydride (60% dispersion in oil) was added to a solution of 3.76 g (9.27 mmol) of compound 23 in 38 ml of tetrahydrofuran, and stirred for 30 minutes to prepare a reactant solution. The foregoing methylene chloride solution of compound 22. was added dropwise thereto while stirring and cooling with ice, and the resulting reaction mixture was stirred for an additional one hour. During the stirring, the reaction solution turned dark orange.

Thereafter, methylene chloride and tetrahydrofuran were distilled away from the reaction solution under reduced pressure, and to the residue methylene chloride was added, washed with a saturated aqueous solution of ammonium chloride, and dried over Glauber's salt. The methylene chloride was distilled away under reduced pressure at a temperature of below 30° C. to obtain 8.40 g of oily matter containing compound 24.

This oily matter was dissolved into 49 ml of ethanol, and 3.1 ml of 28% sodium methylate was added thereto. The reaction solution was heated while stirring under reflux for 11 hours. The ethanol was then distilled away under reduced pressure, and to the residue ethyl acetate was added, washed with a saturated aqueous solution of sodium chloride, and dried over Glauber's salt. Thereafter, the ethyl acetate was distilled away to obtain 5.39 g of oily matter containing exemplified compound (6). This oily matter was purified by silica gel column chromatography (eluate: hexane/ethyl acetate) to yield 1.0 g of exemplified compound (6) as crystals colored slightly by contamination with impurity (yield rate: 22% based on compound 16). Data of physical properties of the thus obtained compound (6) are shown below.

Melting Point: 56° to 59° C.

$^1$H-NMR Spectrum (CDCl$_3$): $\delta = 6$ 0.88 (t, 3H), 1.1 to 1.7 (m, 26H), 1.47 (s, 9H), 2.3 to 2.5 (m, 2H), 2.58 (t, 2H), 3.18 (t, 2H), 4.07 (t, 2H), 6.65 to 6.8 (m, 3H), 7.16 (dd, 1H), 9.08 (brs, 1H).

Mass Spectrum: m/e 585 (M-1)$^+$, (EI-Mass).

In addition, compound 23 was synthesized from compound (b), which had been prepared from cardanol and γ-lactone in a known manner, according to the method described in *Journal of the American Chemical Society*, vol. 76, p. 3209 (1954):

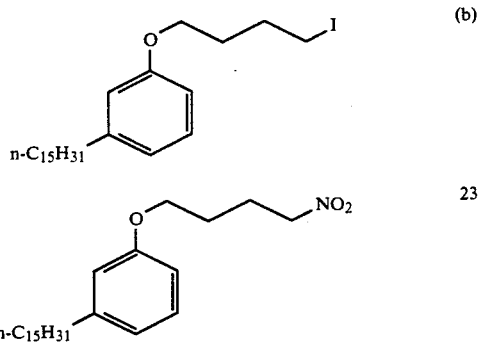

REFERENCE EXAMPLE

Compounds useful as photographic couplers were derived from the 1H-pyrazolo[5,1-c]-1,2,4-triazoles synthesized in accordance with this invention. For instance, the synthesis of coupler (1) illustrated below which is derived from exemplified compound (1) is described below in detail:

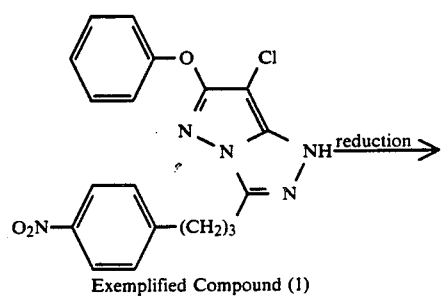

Exemplified Compound (1)

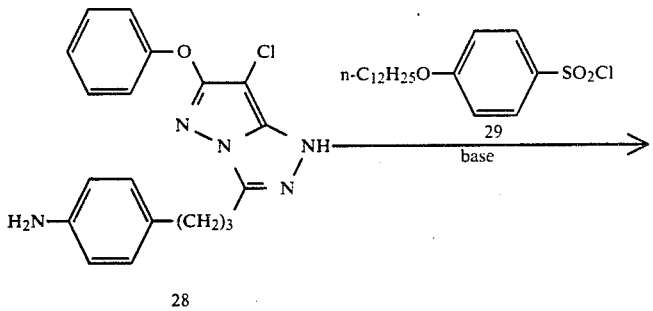

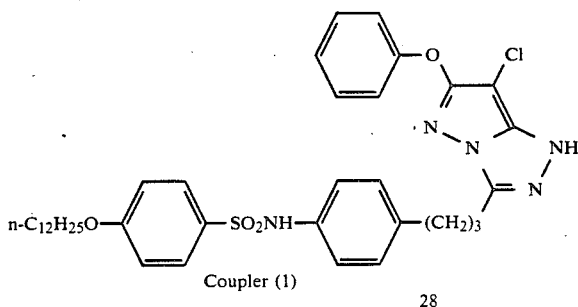

Coupler (1)

Synthesis of Compound 28

4.2 ml of water, 0.13 g ($2.48 \times 10^{-3}$ mol) and 0.14 ml ($2.48 \times 10^{-3}$ mol) of acetic acid were added to 1.38 g ($2.48 \times 10^{-2}$ mol) of reduced iron powder, and the resulting mixture was heated while stirring under reflux for 15 minutes. 13 ml of isopropanol was added thereto, and the heating while stirring under reflux was further continued for 20 minutes. A solution of 1.97 g ($4.95 \times 10^{-3}$ mol) of exemplified compound (1) in 5.9 ml of isopropanol was added dropwise thereto, and heated while stirring under reflux for 2 hours. Thereafter, the reaction solution was filtered using Celite as a filter aid, and the filtrate was diluted with chloroform, washed with a saturated aqueous solution of sodium chloride, and dried over Glauber's salt. The chloroform was distilled away under reduced pressure to obtain 1.70 g of compound 28 as a crude product.

Synthesis of Coupler (1)

5.1 ml of dimethylacetamide was added to a solution of 1.70 g ($4.62 \times 10^{-3}$ mol) of crude compound 28 in 8.5 ml of tetrahydrofuran. 2.17 g ($6.01 \times 10^{-3}$ mol) of compound 29 was added first thereto, followed by the addition of 0.49 ml ($6.01 \times 10^{-3}$ mol) of pyridine while stirring and cooling with ice. The resulting mixture was stirred for 1.5 hours at room temperature, and then diluted with ethyl acetate, washed with a saturated aqueous solution of sodium chloride, and dried over Glauber's salt. Ethyl acetate was distilled away therefrom under reduced pressure to obtain 4.10 g of Coupler (1) as a crude product. The crude product was purified by silica gel column chromatography (eluate: chloroform/ethyl acetate), and recrystallized from hot acetonitrile to yield 1.28 g of Coupler (1) as colorless crystals (yield rate: 37% based on exemplified compound (1)). Data of physical properties of the thus obtained coupler are shown below.

Melting Point: 101° to 102° C.

$^1$H-NMR Spectrum (CDCl$_3$): $\delta = 0.90$ (t, 3H), 1.1 to 1.5 (m, 20H), 1.7 to 1.9 (m, 2H), 2.0 to 2.2 (m, 2H), 2.52 (t, 2H), 2.90 (t, 2H), 3.92 (t, 2H), 6.8 to 7.4 (m, 12H), 7.66 (d, 2H), 9.83 (brs, 1H).

Mass Spectrum: m/e 691 (M$^+$)

Elemental Analysis

Calcd. (as C$_{37}$H$_{46}$N$_5$O$_4$SCl): C 64.19; H 6.70; N 10.12; Cl 5.12; S 4.63.

Found: C 64.24; H 6.64; N 10.01; Cl 5.14; S 4.63

While the invention has been described in detail and with reference to specific embodiments thereof, it will be apparent to one skilled in the art that various changes and modifications can be made therein without departing from the spirit and scope thereof.

What is claimed is:

1. A method of producing 1H-pyrazolo[5,1-c]-1,2,4-triazoles represented by formula (II):

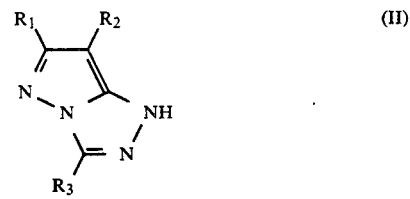

wherein R$_1$, R$_2$, and R$_3$ each represents:
a hydrogen atom,
a halogen atom,
an alkyl or aralkyl group,
an alkyl or aralkyl group substituted with a hydroxyl group, a nitro group, a carboxyl group, a cyano group, halogen atom, a phenyl group or a phenoxy group,
a phenyl group, a 4-t-butylphenyl group, a 2,4-di-t-amylphenyl group, a 4-tetradecanamidophenyl group or a 3-nitrophenyl group,
a 2-furyl group, a 2-thienyl group, a 2-pyrimidinyl group, a 2-benzothiazolyl group, a 1-phenyltetrazole-5-oxy group, a 2-tetrahydropyranyloxy group, a 2-benzothiazolylthio group, a 2,4- diphenoxy-1,3,5-triazole-6-thio group, a 2-pyridylthio group, a triazolyl group, a tetrazolyl group, an imidazolyl group, or a pyrazolyl group, a cyano group, a phenoxy group, a 2-methylphenoxy group, a 4-t-butylphenoxy group, a 3-nitrophenoxy group, a 3-t-butyloxycarbamoylphenoxy group, a 3-methoxycarbamoylphenoxy group, a 2,4-dimethylphenoxy group, a 4-methylphenoxy group, a 2-methoxy-5-nitrophenoxy group or a 2-methoxy-4-nitrophenoxy group, an alkylthio group, a phenylthio group, or an azo group, which comprises making a compound represented by formula (I) undergo a ring closure reaction:

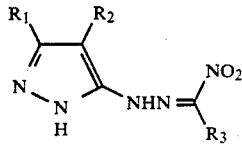

(I)

wherein $R_1$, $R_2$, and $R_3$ are defined above.

2. The method of producing the 1H-pyrazolo[5,1-c]-1,2,4-triazoles of claim 1, wherein $R_2$ is selected from the group consisting of a halogen atom, a phenyloxy group, an alkylthio group, a phenylthio group, an azo group, a triazolyl group, a tetrazolyl group, an imidazolyl group and a pyrazolyl group.

3. The method of producing the 1H-pyrazolo[5,1-c]-1,2,4-triazoles of claim 1, wherein the ring closing reaction is carried out in the presence of a base selected from the group consisting of potassium hydroxide, sodium methoxide, potassium tert-butoxide, sodium hydride, butyl lithium, methylmagnesium iodide, lithium diisopropylamide, sodium, potassium, pyridine, sodium hydroxide and triethylamine.

4. The method of producing the 1H-pyrazolo[5,1-c]-1,2,4-triazoles of claim 3, wherein the amount of the base is from 0.5 to 5 equivalents relative to the amount of the compound represented by formula (I).

5. The method of producing the 1H-pyrazolo[5,1-c]-1,2,4-triazoles of claim 1, wherein the ring closure reaction is conducted in a solvent.

6. The method of producing the 1H-pyrazolo[5,1-c]-1,2,4-triazoles of claim 1, wherein the ring closure reaction is conducted at a temperature of from 10° to 150° C.

7. The method of producing the 1H-pyrazolo[5,1-c]-1,2,4-triazoles of claim 3, wherein said base is selected from the group consisting of sodium hydroxide and sodium methoxide.

* * * * *

UNITED STATES PATENT AND TRADEMARK OFFICE
CERTIFICATE OF CORRECTION

PATENT NO. : 5,110,941

DATED : May 5, 1992

INVENTOR(S) : Taniguchi et al

It is certified that error appears in the above-identified patent and that said Letters Patent is hereby corrected as shown below:

Title Page:
Item [21] Appl. No.: change "423,891" to --423,894--

Signed and Sealed this

Twentieth Day of July, 1993

Attest:

MICHAEL K. KIRK

*Attesting Officer*     Acting Commissioner of Patents and Trademarks